US 7,527,608 B2

(12) United States Patent
Mason

(10) Patent No.: US 7,527,608 B2
(45) Date of Patent: May 5, 2009

(54) MEDICATION INFUSION AND ASPIRATION SYSTEM AND METHOD

(75) Inventor: Jeffrey T. Mason, Escondido, CA (US)

(73) Assignee: LMA North America, Inc., San Diego, CA (US)

( * ) Notice: Subject to any disclaimer, the term of this patent is extended or adjusted under 35 U.S.C. 154(b) by 147 days.

(21) Appl. No.: 10/909,157

(22) Filed: Jul. 30, 2004

(65) Prior Publication Data

US 2007/0078377 A1    Apr. 5, 2007

Related U.S. Application Data

(63) Continuation-in-part of application No. 10/218,106, filed on Aug. 12, 2002, now Pat. No. 6,893,414.

(51) Int. Cl.
*A61M 1/00* (2006.01)
*F04B 39/00* (2006.01)
*F04B 53/00* (2006.01)

(52) U.S. Cl. ................................. 604/151; 417/477.2

(58) Field of Classification Search ......... 604/131–135, 604/151–153, 246, 65–67, 892.1, 6.11; 417/477.2–477.14
See application file for complete search history.

(56) References Cited

U.S. PATENT DOCUMENTS

| | | | |
|---|---|---|---|
| 3,908,657 A * | 9/1975 | Kowarski | 600/580 |
| 3,920,014 A | 11/1975 | Banko | |
| 4,070,725 A | 1/1978 | Austin et al. | |
| 4,177,810 A | 12/1979 | Gourlandt | |
| 4,180,067 A | 12/1979 | Derlien | |
| 4,180,074 A | 12/1979 | Murry et al. | |
| 4,193,397 A | 3/1980 | Tucker et al. | |
| 4,217,894 A | 8/1980 | Franetzki | |
| 4,231,287 A | 11/1980 | Smiley | |
| 4,258,711 A | 3/1981 | Tucker et al. | |
| 4,273,121 A | 6/1981 | Jassawalla | |
| 4,276,004 A | 6/1981 | Hahn | |
| 4,278,085 A | 7/1981 | Shim | |
| 4,300,554 A | 11/1981 | Hessberg et al. | |

(Continued)

FOREIGN PATENT DOCUMENTS

EP    1430924 A1    6/2004

(Continued)

*Primary Examiner*—Kevin C Sirmons
*Assistant Examiner*—Elizabeth R MacNeill
(74) *Attorney, Agent, or Firm*—David W. Meibos; Barbara Daniels; Daniel F. Justin

(57) ABSTRACT

A medication infusion system may include a controller and a reservoir module including a reservoir containing medication to be delivered to an internal wound site via the controller. The controller may have a peristaltic pump driven by a motor to urge medication to flow toward the internal wound site. The controller and the reservoir module may each have a mating surface oriented such that the reservoir module can slide into engagement with the controller along a direction parallel to an axis of rotation of the motor. The mating surfaces may have features such as dovetails that facilitate secure assembly and retention. A reservoir module may include only a single reservoir for infusion, or two separate reservoirs for infusion and aspiration. One single controller may be capable of mating with either type of reservoir module to provide only infusion, or infusion combined with aspiration, as desired.

35 Claims, 6 Drawing Sheets

U.S. PATENT DOCUMENTS

| | | | |
|---|---|---|---|
| 4,308,866 A | 1/1982 | Jelliffe et al. | |
| 4,332,246 A | 6/1982 | Thomson | |
| 4,335,835 A | 6/1982 | Beigler et al. | |
| 4,355,638 A | 10/1982 | Iwatschenko et al. | |
| 4,395,259 A | 7/1983 | Prestele et al. | |
| 4,396,385 A | 8/1983 | Kelly et al. | |
| 4,398,910 A | 8/1983 | Blake et al. | |
| 4,468,216 A | 8/1984 | Muto | |
| 4,469,481 A | 9/1984 | Kobayashi | |
| 4,479,797 A | 10/1984 | Kobayashi et al. | |
| 4,496,343 A | 1/1985 | Prosl et al. | |
| 4,519,792 A | 5/1985 | Dawe | |
| 4,525,164 A | 6/1985 | Loeb et al. | |
| 4,526,574 A * | 7/1985 | Pekkarinen | 604/505 |
| 4,559,045 A | 12/1985 | Danby et al. | |
| 4,604,090 A | 8/1986 | Reinicke | |
| 4,619,643 A | 10/1986 | Bai | |
| 4,623,329 A | 11/1986 | Drobish et al. | |
| 4,648,872 A | 3/1987 | Kamen | |
| 4,650,469 A | 3/1987 | Berg et al. | |
| 4,652,260 A | 3/1987 | Fenton, Jr. et al. | |
| 4,653,987 A | 3/1987 | Tsuji et al. | |
| 4,657,486 A | 4/1987 | Stempfle et al. | |
| 4,657,490 A | 4/1987 | Abbott | |
| 4,668,220 A | 5/1987 | Hawrylenko | |
| 4,681,563 A | 7/1987 | Deckert et al. | |
| 4,681,566 A | 7/1987 | Fenton, Jr. et al. | |
| 4,687,475 A | 8/1987 | Tai et al. | |
| 4,692,141 A | 9/1987 | Mahurkar | |
| 4,692,153 A | 9/1987 | Berlin et al. | |
| 4,696,671 A | 9/1987 | Epstein et al. | |
| 4,706,368 A | 11/1987 | Crissman, III et al. | |
| 4,710,166 A | 12/1987 | Thompson et al. | |
| 4,722,734 A * | 2/1988 | Kolln | 604/151 |
| 4,756,706 A | 7/1988 | Kerns et al. | |
| 4,795,439 A | 1/1989 | Guest | |
| 4,798,590 A | 1/1989 | O'Leary et al. | |
| 4,802,885 A | 2/1989 | Weeks et al. | |
| 4,813,937 A | 3/1989 | Vaillancourt | |
| 4,828,545 A | 5/1989 | Epstein et al. | |
| 4,840,542 A | 6/1989 | Abbott | |
| 4,840,620 A | 6/1989 | Kobayashi et al. | |
| 4,846,637 A | 7/1989 | Alderson et al. | |
| 4,900,305 A | 2/1990 | Smith et al. | |
| 4,935,010 A | 6/1990 | Cox et al. | |
| 4,966,585 A | 10/1990 | Gangemi | |
| 4,976,590 A | 12/1990 | Baldwin | |
| 4,978,335 A | 12/1990 | Arthur, III | |
| 5,004,455 A | 4/1991 | Greenwood et al. | |
| 5,011,469 A * | 4/1991 | Buckberg et al. | 604/6.11 |
| 5,017,059 A | 5/1991 | Davis | |
| 5,019,047 A | 5/1991 | Kriesel | |
| 5,024,663 A | 6/1991 | Yum | |
| 5,045,075 A | 9/1991 | Ersek | |
| 5,046,486 A | 9/1991 | Grulke et al. | |
| 5,053,023 A | 10/1991 | Martin | |
| 5,059,174 A | 10/1991 | Vaillancourt | |
| 5,073,164 A | 12/1991 | Hollister et al. | |
| 5,078,683 A | 1/1992 | Sancoff et al. | |
| 5,098,387 A | 3/1992 | Wiest et al. | |
| 5,106,374 A | 4/1992 | Apperson et al. | |
| 5,116,310 A | 5/1992 | Seder et al. | |
| 5,135,498 A | 8/1992 | Kam et al. | |
| 5,167,623 A | 12/1992 | Cianci et al. | |
| 5,169,389 A | 12/1992 | Kriesel | |
| 5,178,609 A | 1/1993 | Ishikawa | |
| 5,180,365 A | 1/1993 | Ensminger et al. | |
| 5,188,603 A | 2/1993 | Vaillancourt | |
| 5,207,642 A | 5/1993 | Orkin et al. | |
| 5,242,407 A | 9/1993 | Struble et al. | |
| 5,244,463 A | 9/1993 | Cordner, Jr. et al. | |
| 5,246,347 A | 9/1993 | Davis | |
| 5,249,937 A * | 10/1993 | Aubert | 417/475 |
| 5,266,013 A * | 11/1993 | Aubert et al. | 417/474 |
| 5,279,568 A | 1/1994 | Cater | |
| 5,399,166 A | 3/1995 | Laing | |
| 5,431,634 A | 7/1995 | Brown | |
| 5,433,704 A | 7/1995 | Ross et al. | |
| 5,451,215 A | 9/1995 | Wolter | |
| 5,472,317 A | 12/1995 | Field et al. | |
| 5,472,420 A | 12/1995 | Campbell | |
| 5,480,380 A | 1/1996 | Martin | |
| 5,480,386 A | 1/1996 | Brohy et al. | |
| 5,503,538 A | 4/1996 | Wiernicki et al. | |
| 5,514,103 A | 5/1996 | Srisathapat et al. | |
| 5,522,803 A | 6/1996 | Teissen-Simony | |
| 5,547,472 A | 8/1996 | Onishi et al. | |
| 5,554,114 A | 9/1996 | Wallace et al. | |
| 5,558,639 A * | 9/1996 | Gangemi et al. | 604/67 |
| 5,584,811 A | 12/1996 | Ross et al. | |
| 5,616,121 A * | 4/1997 | McKay | 604/35 |
| 5,658,252 A | 8/1997 | Johnson | |
| 5,665,061 A * | 9/1997 | Antwiler | 604/6.07 |
| 5,672,167 A | 9/1997 | Athayde et al. | |
| 5,681,283 A | 10/1997 | Brownfield | |
| 5,695,464 A | 12/1997 | Viallet | |
| 5,718,692 A | 2/1998 | Schon et al. | |
| 5,728,069 A | 3/1998 | Montevecchi et al. | |
| 5,733,319 A * | 3/1998 | Neilson et al. | 607/105 |
| 5,738,659 A | 4/1998 | Neer et al. | |
| 5,743,878 A | 4/1998 | Ross et al. | |
| 5,746,717 A | 5/1998 | Aigner | |
| 5,746,719 A | 5/1998 | Farra et al. | |
| 5,749,854 A | 5/1998 | Shen | |
| 5,755,691 A | 5/1998 | Hilborne | |
| 5,755,692 A | 5/1998 | Manicom | |
| 5,769,824 A | 6/1998 | Hjertman et al. | |
| 5,776,104 A | 7/1998 | Guignard et al. | |
| 5,782,805 A | 7/1998 | Meinzer et al. | |
| 5,791,880 A | 8/1998 | Wilson | |
| 5,795,326 A | 8/1998 | Siman | |
| 5,797,869 A | 8/1998 | Martin et al. | |
| 5,797,881 A | 8/1998 | Gadot | |
| 5,817,052 A | 10/1998 | Johnson et al. | |
| 5,882,339 A * | 3/1999 | Beiser et al. | 604/153 |
| 5,891,101 A | 4/1999 | Wilcox et al. | |
| 5,904,666 A | 5/1999 | DeDecker et al. | |
| 5,916,165 A | 6/1999 | Duchon et al. | |
| 5,938,638 A | 8/1999 | Passariello et al. | |
| 5,947,928 A | 9/1999 | Muller | |
| 5,947,953 A | 9/1999 | Ash et al. | |
| 5,954,696 A | 9/1999 | Ryan | |
| 5,957,889 A | 9/1999 | Poulsen et al. | |
| 5,957,890 A | 9/1999 | Mann et al. | |
| 5,961,485 A | 10/1999 | Martin | |
| 5,968,009 A | 10/1999 | Siman | |
| 5,968,014 A | 10/1999 | Neftel et al. | |
| 5,976,103 A | 11/1999 | Martin | |
| 5,976,109 A | 11/1999 | Heruth | |
| 5,989,206 A | 11/1999 | Prosl et al. | |
| 6,001,079 A | 12/1999 | Pourchez | |
| 6,007,518 A | 12/1999 | Kriesel et al. | |
| 6,048,328 A | 4/2000 | Haller et al. | |
| 6,056,718 A | 5/2000 | Funderburk et al. | |
| 6,059,767 A | 5/2000 | Noriega | |
| 6,086,575 A | 7/2000 | Mejslov | |
| 6,090,061 A * | 7/2000 | Steuer et al. | 604/4.01 |
| 6,113,574 A | 9/2000 | Spinello | |
| 6,132,415 A | 10/2000 | Finch et al. | |
| 6,149,621 A | 11/2000 | Makihara | |
| 6,190,349 B1 | 2/2001 | Ash et al. | |
| 6,190,359 B1 | 2/2001 | Heruth | |
| 6,193,704 B1 | 2/2001 | Winters | |
| 6,200,292 B1 | 3/2001 | French et al. | |

| | | | | | | |
|---|---|---|---|---|---|---|
| 6,206,849 | B1 | 3/2001 | Martin et al. | 6,348,043 B1 | 2/2002 | Hagen et al. |
| 6,210,361 | B1 | 4/2001 | Kamen et al. | 6,742,992 B2 | 6/2004 | Davis |
| 6,217,556 | B1 | 4/2001 | Ellingson et al. | 7,168,930 B2 * | 1/2007 | Cull et al. ............... 417/477.8 |
| 6,248,093 | B1 | 6/2001 | Moberg | 2001/0025168 A1 | 9/2001 | Gross et al. |
| 6,248,100 | B1 | 6/2001 | de Toledo et al. | 2001/0056259 A1 | 12/2001 | Skinkle et al. |
| 6,264,624 | B1 | 7/2001 | Desmond, III et al. | 2002/0016570 A1 | 2/2002 | Cartledge |
| 6,270,478 | B1 | 8/2001 | Mern.o slashed.e | 2002/0019612 A1 | 2/2002 | Watanabe et al. |
| 6,270,490 | B1 | 8/2001 | Hahnen | | | |
| 6,280,399 | B1 | 8/2001 | Rossin et al. | | | |

FOREIGN PATENT DOCUMENTS

| | | | |
|---|---|---|---|
| 6,290,690 B1 | 9/2001 | Huculak et al. | |
| EP | | 1073494 B1 | 7/2004 |
| 6,299,598 B1 | 10/2001 | Bander | |
| FR | | 2753103 A1 * | 3/1998 |
| 6,299,601 B1 | 10/2001 | Hjertman | |
| WO | | WO03028798 A1 | 4/2003 |
| 6,302,864 B1 | 10/2001 | Nowosielski | |
| WO | | WO2004058334 A1 | 7/2004 |
| 6,312,227 B1 | 11/2001 | Davis | |
| WO | | WO2004058337 A1 | 7/2004 |
| 6,319,222 B1 | 11/2001 | Andrew et al. | |
| 6,325,788 B1 | 12/2001 | McKay | |

\* cited by examiner

MEDICATION INFUSION AND ASPIRATION SYSTEM AND METHOD

CROSS-REFERENCE TO RELATED APPLICATIONS

This application is a continuation-in-part of U.S. application Ser. No. 10/218,106, filed Aug. 12, 2002 now U.S. Pat. No. 6,893,414 and entitled INTEGRATED INFUSION AND ASPIRATION SYSTEM AND METHOD, the disclosure of which is incorporated herein by reference.

BACKGROUND OF THE INVENTION

1. The Field of the Invention

The present invention relates generally to the post-surgical treatment of closed wounds and specifically to methods and systems for infusion of a wound site to manage pain, swelling, bleeding and infection.

2. The Relevant Technology

One of the most difficult aspects of enduring a major surgical procedure is coping with the post-operative pain and swelling. Commonly, opioid analgesics, sometimes referred to as narcotics, are administered post-operatively to counter the pain associated with wound healing and recovery. However, the use of systemic opioid analgesics, whether administered by oral, intramuscular, or intravenous methods, includes a host of possible undesirable side effects, including: respiratory depression, renal function depression, nausea, constipation, ataxia, confusion, sweating, and itching. The length of hospital stay for patients undergoing a major surgical procedure is, in part, determined by the need to monitor and control the side effects of systemically administered opioid analgesics.

More recently, infusion pumps have been used to percutaneously deliver local anesthetics directly to the surgical wound. Thus, many of the undesirable side effects of systemic opioid analgesics are avoided. Furthermore, medication dosage is considerably less than systemic delivery since the medication is delivered directly to the affected site. However, contemporary percutaneous pain medication infusion pumps do not provide consistent relief of pain. Furthermore, many currently available medication infusion pumping arrangements are unable to adequately aspirate the affected site to reduce fluid build-up and swelling.

Yet further, many medication infusion pumps are somewhat complex and/or difficult to assemble. Some such pumps may not have a mechanism by which the infusion reservoir can be sufficiently secured to the pump. Furthermore, a single controller is typically usable with only one type of reservoir module. Due to the lack of interchangeability among controllers and medication reservoir modules, a medical professional may need to choose between multiple controllers, depending on factors such as whether aspiration is needed. Accordingly, the process assembling and operating a medication infusion pumping arrangement is somewhat more complicated than is desirable.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
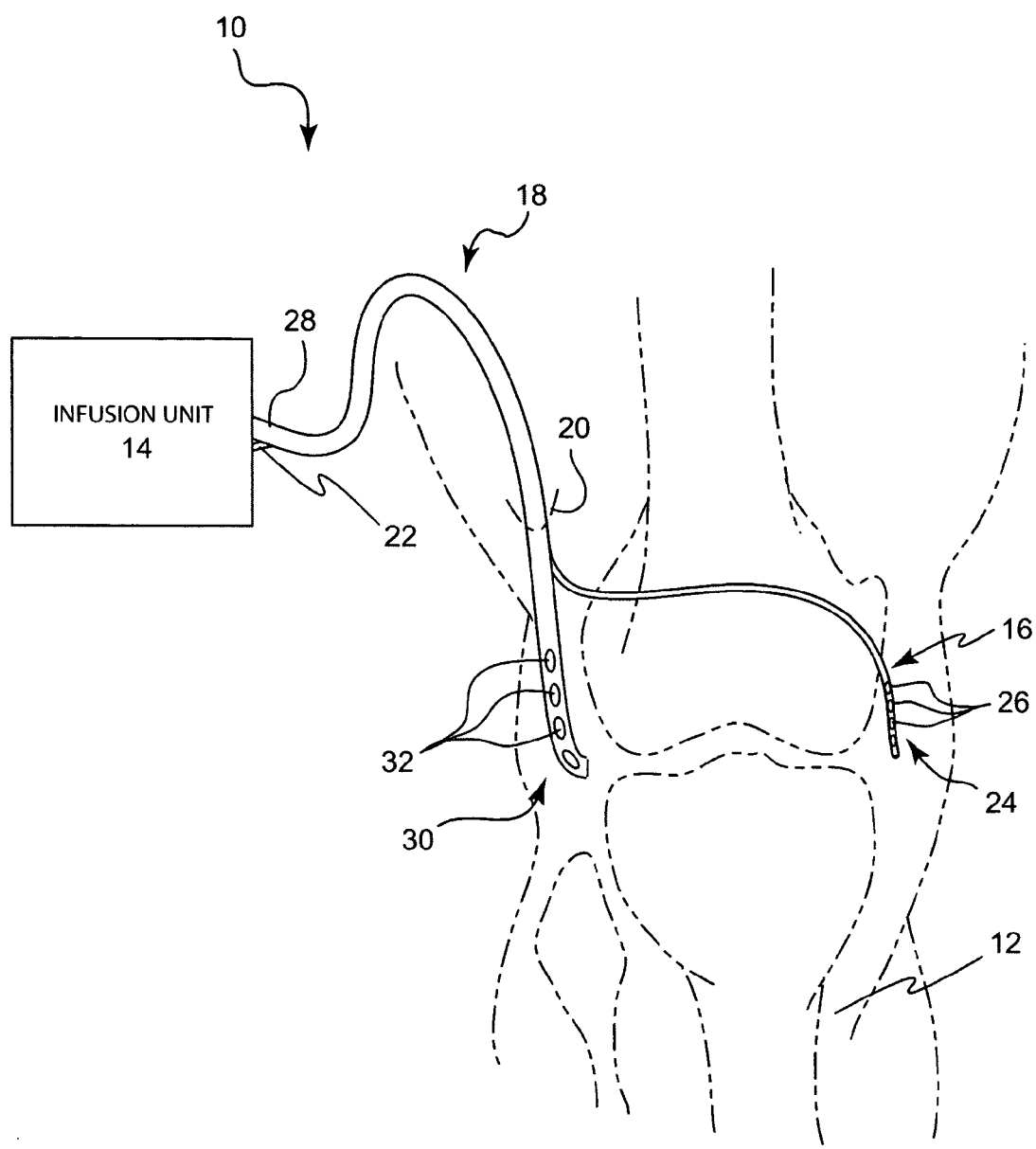
FIG. 1 is a schematic view of an integrated infusion and aspiration system applied to the knee of a patient.

Referring to FIG. 1, a schematic view illustrates an integrated infusion and aspiration system 10, or system 10, according to one embodiment of the invention. The system 10 may be postoperatively used to provide pain relief medication directly to an internal wound site 12. In FIG. 1, the internal wound site 12 is a knee that has been surgically treated, for example, via a partial or total knee arthroplasty. However, the systems and methods of the present invention are not limited to postoperative use, and may be used to relieve pain before or after treatment of injury to any part of the body. In addition to providing pain relief medication to the internal wound site 12, the system 10 aspirates internal fluids, such as spent medication and biological fluids, from the internal wound site 12.

In the embodiment of FIG. 1, the system 10 includes an integrated infusion and aspiration unit 14, hereinafter referred to as an infusion unit 14, that provides pressurized medication and provides a corresponding relative vacuum to receive fluids aspirated from the internal wound site 12. Additionally, the system 10 includes an infusion catheter 16 through which medication is delivered to the internal wound site 12, and an aspiration catheter 18 through which fluids are received in the infusion unit 14 from the internal wound site 12. As shown, a portion of the infusion catheter 16 may be nested within a corresponding portion of the aspiration catheter 18 so that both catheters 16, 18 gain access to the internal wound site 12 through a single point-of-entry 20.

As illustrated, the infusion catheter 16 has a proximal end 22 and a distal end 24, with a plurality of flow orifices 26 arrayed along the distal end 24 to provide infusion of medication along a relatively broad dispersal path within the internal wound site 12. Similarly, the aspiration catheter 18 has a proximal end 28 and a distal end 30, with a plurality of flow orifices 32 arranged along the distal end 30 to receive fluids from a relatively broad area of the internal wound site 12. The proximal end 22 of the infusion catheter 16 is generally nested within the proximal end 28 of the aspiration catheter 18 so that medication moves toward the internal wound site 12 through the infusion catheter 16, and fluids are removed from the internal wound site 12 through the distal end 30 of the aspiration catheter 18, and then through the generally annular space between the proximal ends 22, 28 of the catheters 16, 18.

Figure 2:
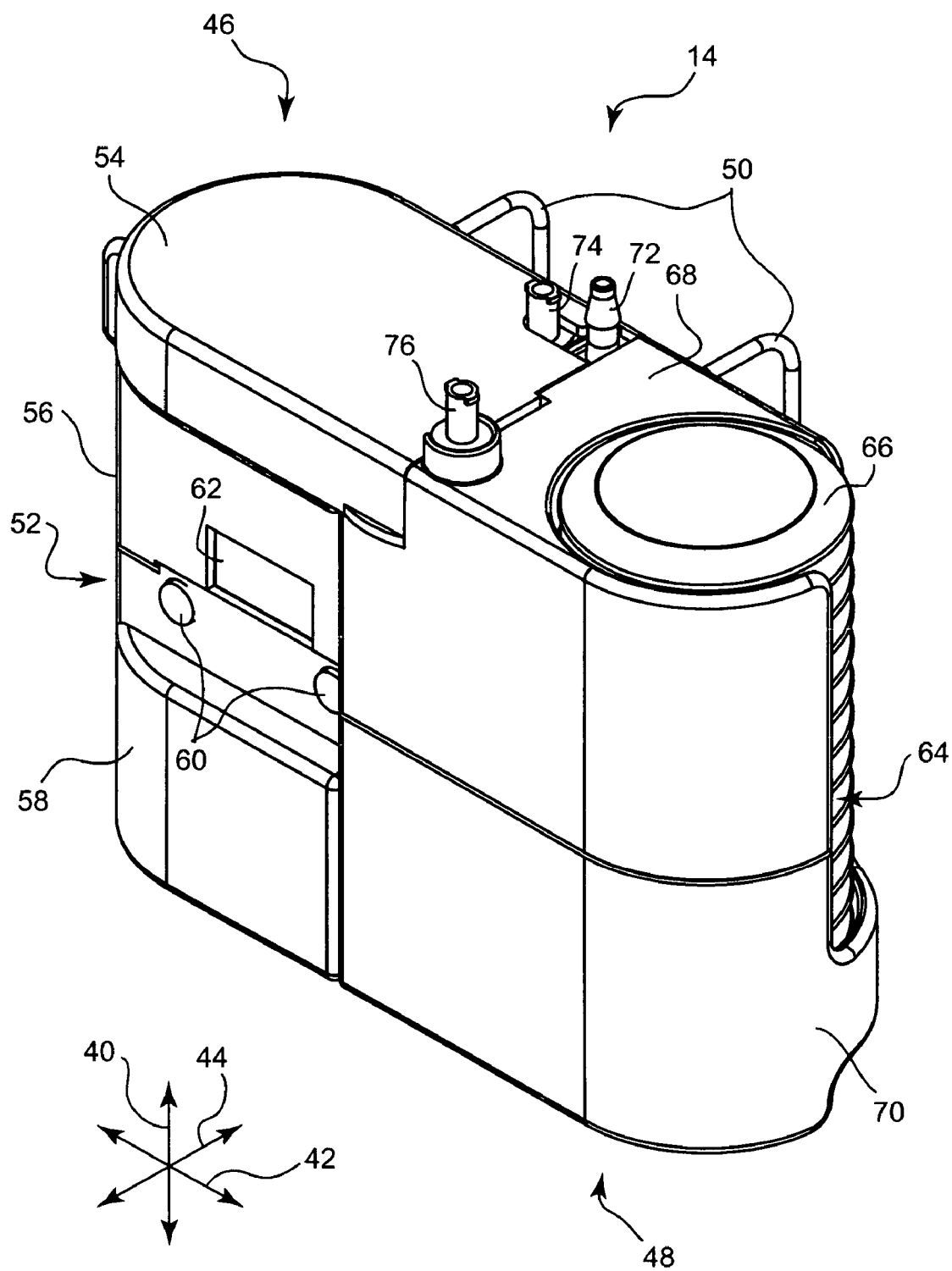
FIG. 2 is a perspective view of an infusion unit of the integrated infusion and aspiration system of FIG. 1, in a fully-assembled state.

Referring to FIG. 2, a perspective view illustrates the infusion unit 14 of the system 10 of FIG. 1, without the catheters 16, 18. The infusion unit 14 has a longitudinal direction 40, a lateral direction 42, and a transverse direction 44, which are oriented as illustrated by the arrows in FIG. 2. The infusion unit 14 has a controller 46 and a reservoir module 48. The reservoir module 48 contains medication to be provided to the internal wound site 12 and fluids aspirated from the internal wound site 12. The controller 46 provides the necessary pressure differentials to control infusion of medication to the internal wound site 12 and aspiration of fluids from the internal wound site 12. The infusion unit 14 may also have a pair of mounting brackets 50 or other attachment devices that can be used to attach the infusion unit 14 to a mobile rack, hospital bed frame, or other piece of hospital equipment.

The controller 46 has a main body 52 that contains most of the internal components (not shown) of the controller 46, and a cap 54 that can be removed to couple the controller 46 to the reservoir module 48 in a manner that will be shown and described in greater detail subsequently. The main body 52 has a first portion 56 and a second portion 58 that are attached together via relative motion in the longitudinal direction 40 to encase the internal components, as will also be shown and described in greater detail. The controller 46 has controls such as buttons 60 that can be used by medical personnel to control the operation of the controller 46. Additionally, the controller 46 may have a display 62 that may show information such as infusion and aspiration history, the current operational mode of the controller 46, and the like.

The reservoir module 48 has a reservoir retainer 64 that serves to retain a first reservoir (not shown in FIG. 2) and a second reservoir 66. The first reservoir contains medication to be infused into the internal wound site 12 and the second reservoir 66 receives fluid aspirated from the internal wound site 12. The second reservoir 66 may have a bellows-like shape with side walls that are compactable along the longitudinal direction 40. The side walls are resilient, and therefore tend to push the ends of the second reservoir 66 away from each other to form a vacuum within the second reservoir 66. The vacuum acts through the aspiration catheter 18 to withdraw fluids from the internal wound site 12.

The reservoir retainer 64 has a first portion 68 and a second portion 70 that are attached together along the longitudinal direction 40 in a manner similar to that of the first and second portions 56, 58 of the main body 52 of the controller 46. Additionally, the reservoir module 48 has an infusion port 72 shaped to be connected to the proximal end 22 of the infusion catheter 16 and an aspiration port 74 shaped to be connected to the proximal end 28 of the aspiration catheter 18. A fill port 76 is shaped to be connected to a supply of medication to enable the first reservoir to be filled without removing it from the reservoir retainer 64.

The controller 46 and the reservoir module 48 are coupled together in a manner that is simple and relatively failsafe. The manner in which the controller 46 and reservoir module 48 are coupled together will be shown and described in greater detail with reference to FIG. 3, as follows.

Figure 3:
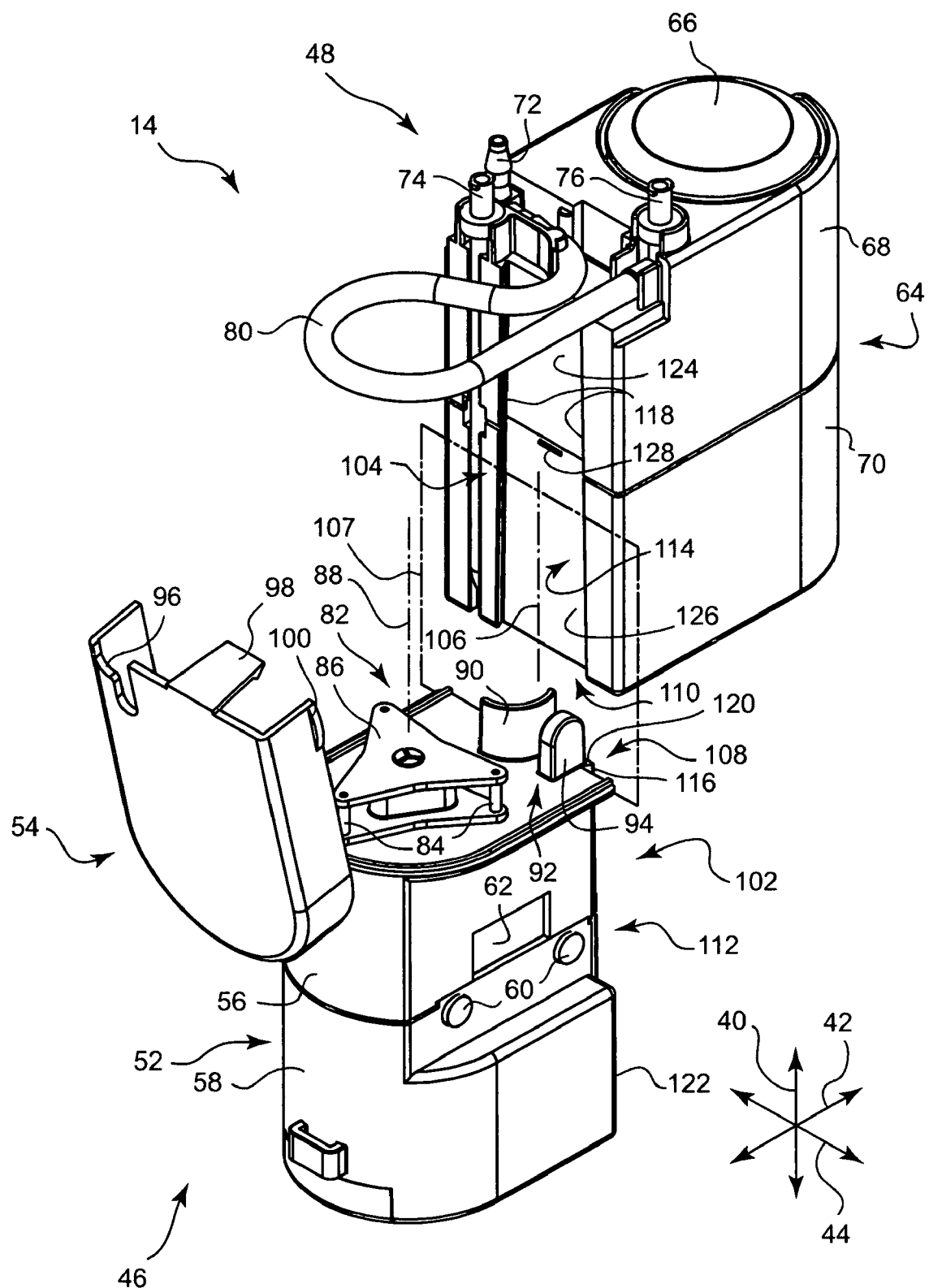
FIG. 3 is an exploded, perspective view of the infusion unit of FIG. 1.

Referring to FIG. 3, an exploded, perspective view illustrates the infusion unit 14 of FIG. 1. In FIG. 3, the reservoir module 48 has been removed from the controller 46 and the cap 54 of the controller 46 has been removed from the main body 52. As shown, the reservoir module 48 has a conduit, which may take the form of a tube 80, that extends in a generally circular pathway from a location in communication with the fill port 76 to convey medication to the infusion port 72. In this application, the term "conduit" refers to a fluid conveying structure with any cross sectional shape. Accordingly, a "conduit" need not necessarily be a tube.

The controller 46 has a pump 82, which may take the form of a peristaltic pump designed to compress a portion of the tube 80 and to move the compressed portion along the tube 80 to urge the medication to move through the tube 80 in a highly controllable manner. The pump 82 may include a plurality of rotors 84 retained by a rotor carriage 86 that rotates about an axis of rotation 88 to move the rotors 84 along a circular path. The rotor carriage 86 is driven by a motor (not shown in FIG. 3) that provides rotational output about the axis of rotation 88. The rotors 84 may take the form of small-diameter cylindrical rollers that are able to roll along the exterior of the tube 80. The tube 80 may be stretched tightly around the rotors 84 such that the tube 80 is pinched relatively tightly proximate each of the rotors 84, so that medication is generally unable to flow into the infusion catheter 16 in the absence of motion of the rotors 84.

The present invention envisions the use of a wide variety of different types of pumps. For example, peristaltic pumps need not involve stretching of a conduit about the rotors, but may instead be based upon compression of the conduit by the rotors against an opposing surface, such as a generally cylindrical interior wall. Indeed, a controller according to the present invention need not have a peristaltic pump, but may instead use a different type of pump such as a screw pump, a rotary vane pump, a rod-and-piston pump, or any other known type of pump.

The controller 46 also has a constraining member in the form of an arcuate wall 90 that abuts a portion of the tube 80 to control the path of the tube 80 around the rotors 84. The arcuate wall 90 also causes the tube 80 to assume a generally oval cross section proximate the arcuate wall to enhance the operation of a blockage sensor 92. The blockage sensor 92 is designed to sense preferential distention of the portion of the tube 80 proximate the arcuate wall 90 to determine whether the tube 80 or the infusion catheter 16 has been pinched or blocked. Accordingly, the blockage sensor 92 includes a switch 94 that either closes or opens a circuit in response to abnormal distention of the tube 80. Closing or opening the circuit may trigger cessation of infusion and/or aspiration, production of an audible alarm tone, or the like.

The cap 54 is generally shaped to cover the tube 80, the rotors 84, and the rotor carriage 86 to prevent external objects from interfering with the operation of the pump 82. The cap 54 has an alcove 96 shaped to adjoin the infusion and aspiration ports 72, 74 such that the infusion and aspiration ports 72, 74 are able to extend through the space covered by the cap 54. The cap 54 also has a locking tab 98, which may snap into engagement with the main body 52 of the controller 46 to keep the cap attached to the main body 52 until a threshold removal force is applied. The cap 54 also has a release tab 100 that may be pressed by a finger or thumb to facilitate removal of the cap 54 from the main body 52.

The controller 46 and the reservoir module 48 are easily attachable to each other. The controller 46 has a mating surface 102, and the reservoir module 48 has a mating surface 104 with a shape complementary to that of the mating surface 102 of the controller 46. The mating surfaces 102, 104 each extend along the longitudinal direction 40, or more precisely, the mating surfaces 102, 104 extend generally within planes perpendicular to the lateral direction 42. The mating surfaces 102, 104 are shaped such that they can be attached together via relative motion along an attachment direction 106 that extends along the longitudinal direction 40. The attachment direction 106 also extends substantially parallel to the axis of rotation 88 of the rotor carriage 86 and the motor that drives the pump 82. In this phrase, "substantially parallel" does not require precise parallelism, but rather encompasses objects that are angularly offset from each other by as much as 10°, or perhaps even more.

In this application, the term "mate" refers to any process by which two objects are rigidly, but not necessarily inseparably, coupled together. The phrase "mating surface" broadly refers to any surface designed to retain another surface. Although the mating surfaces 102, 104 are generally planar, alternative embodiments may include mating surfaces with a variety of shapes. A mating surface also need not provide for a large area of contact between mating parts, but may instead have one or more relatively small points of attachment. A "generally planar shape" includes surfaces with features that do not protrude excessively. Accordingly, a surface with a dovetail formed therein may have a generally planar shape.

In the embodiment of FIG. 3, the mating surfaces 102, 104 are attached along the attachment direction 106, which is generally parallel to the longitudinal direction 40. In alternative embodiments, mating surfaces could be configured to attach to each other along any direction within a plane, such as an attachment plane 107 illustrated in FIG. 3. Thus, in alternative embodiments, a controller and a reservoir module may be coupled together via relative motion along the transverse direction 44, or via relative motion along a direction with both longitudinal and transverse components.

Returning to the embodiment of FIG. 3, in order to enable the mating surfaces 102, 104 to adhere to each other, the mating surface 102 of the controller 46 has a dovetail feature 108, and the mating surface 104 of the reservoir module 48 has a dovetail feature 110 with a shape complementary to that of the dovetail feature 108 of the controller 46. In this application, a "dovetail feature" is a shaped feature that causes interlocking in response to relative sliding. The dovetail feature 102 of the controller 46 has a central plateau 112, the edge of which is visible in FIG. 3. The dovetail feature 104 of the reservoir module 48 has a central recess 114 shaped to receive the central plateau 112.

The central plateau 112 has two flared edges 116, only one of which is visible in FIG. 3. A "flared edge" is an edge of a feature that extends from another surface at a nonperpendicular angle. The flared edges 116 provide the central plateau 112 with a generally trapezoidal cross section, with the smaller end adjoining the remainder of the controller 46 and the larger end facing toward the reservoir module 48. Similarly, the central recess 114 has two flared edges 118 that provide the central recess 114 with a generally trapezoidal cross section, with the smaller end toward the controller 46. The flared edges 116 cause the dovetail features 108, 110 to engage each other in such a manner that the controller 46 and reservoir module 48 can only be disengaged via relative motion along the longitudinal direction 40. The engaged mating surfaces 102, 104 are unable to move significantly with respect to each other along the lateral direction 42 or the transverse direction 44.

The central plateau 112 and the central recess 114 may be shaped such that the reservoir module 48 can only slide into engagement with the controller 46 from along one direction, i.e., from the relative position illustrated in FIG. 3. More precisely, the central plateau 112 may have a first end 120 and a second end 122, and the central plateau 112 tapers such that the central plateau 112 is narrower at the first end 120 than at the second end 122, along the transverse direction 44. Similarly, the central recess 114 has a fist end 124 and a second end 126, and the first end 124 is narrower than the second end 126 along the transverse direction 44.

Accordingly, as the central plateau 112 slides along the longitudinal direction 40 into the central recess 114, the clearance between the flared edges 116 of the central plateau 112 and the flared edges 118 of the central recess 114 decreases gradually so that the dovetail features 108, 110 fit relatively snugly together when the controller 46 and the reservoir module 48 are longitudinally aligned as shown in FIG. 2. The tapered shapes of the central plateau 112 and the central recess 114 prevents the reservoir module 48 from sliding past too far with respect to the controller 46.

Additionally, the mating surfaces 102, 104 may have locking features that cause the mating surfaces 102, 104 to snap into engagement with each other when the relative positioning of FIG. 2 has been obtained. For example, the central recess 114 may have a locking recess 128 that has a slot-like shape. The locking recess 128 may receive a nub (not visible in FIG. 3) protruding from the central plateau 112 such that, when the relative positioning of FIG. 2 has been obtained, the reservoir module 48 snaps into engagement with the controller 46. The reservoir module 48 and the controller 46 are maintained in the desired relative position until a threshold force is applied longitudinally between the controller 46 and the reservoir module 48 to release the nub from the locking recess 128, thereby permitting the reservoir module 48 to slide longitudinally out of engagement with the controller 46.

Figure 4:
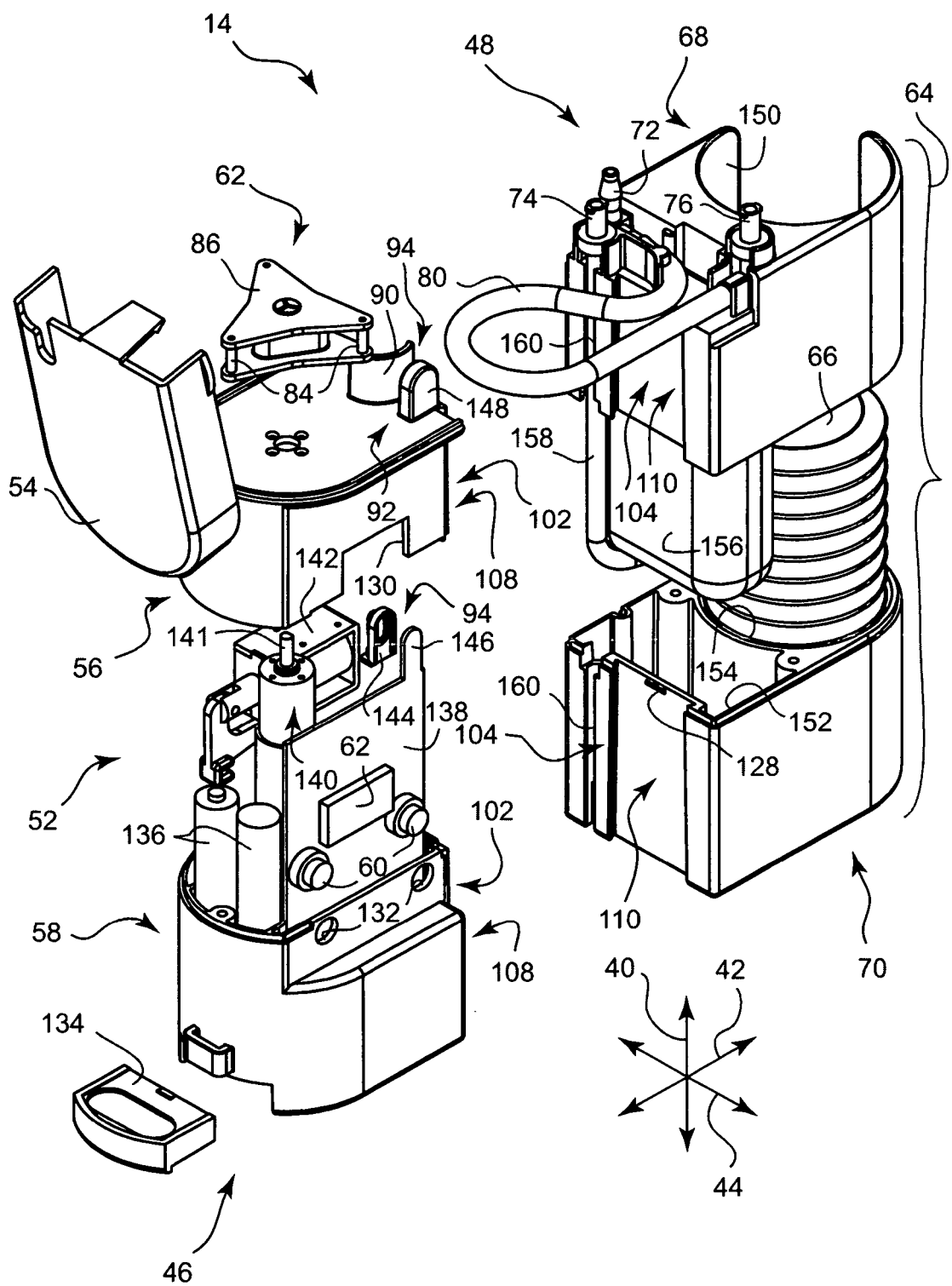
FIG. 4 is an further exploded, perspective view of the infusion unit of FIG. 1.

Referring to FIG. 4, a further exploded perspective view illustrates the infusion unit 14 of FIG. 1. In FIG. 4, the controller 46 and the reservoir module 48 are each exploded to reveal internal components. The first and second portions 56, 58 of the main body 52 of the controller 46 have been withdrawn from each other along the longitudinal direction 40, and the first and second portions 68, 70 of the reservoir retainer 64 have similarly been withdrawn from each other along the longitudinal direction 40.

As shown, the first portion 56 of the main body 52 has an alcove 130 shaped to fit around the display 62 of the controller. Similarly, the second portion 58 of the main body 52 has a pair of holes 132 through which the buttons 60 are able to protrude. The second portion 58 also has a battery cover 134 that is detachable to provide access to a plurality of batteries 136 that supply electrical power to the controller 46. The first and second portions 56, 58 generally contain a circuit board 138 on which a variety of electrical components may be mounted.

A motor 140 adjacent to the circuit board 138 drives the pump 82 by rotating the rotor carriage 86 about the axis of rotation 88 (shown in FIG. 3). The motor 140 has an output shaft 141 that connects to the rotor carriage 86 to transmit torque from the motor 140 to the rotor carriage 86. In the embodiment of FIG. 4, the output shaft 141 is part of the motor 140 and extends directly from the motor to rotate about the axis of rotation 88. However, in alternative embodiments, a transmission could be used to offset an output shaft from the axis of rotation of the motor that drives it. Alternatively, a transmission may permit an output shaft to be oriented differently from the axis of rotation of the motor that drives it. In such embodiments, the reservoir retainer may optionally be attached to the controller along an attachment plane that extends parallel to the output shaft rather than extending parallel to the axis of rotation of the motor.

In addition to the motor 140, the controller 46 may also contain a solenoid unit 142 positioned adjacent to the motor 140. The solenoid unit 142 controls the flow of fluid into the second reservoir 66, thereby controlling aspiration of fluids from the internal wound site 12. The operation of the solenoid unit 142 will be set forth in greater detail subsequently.

As embodied in FIG. 4, the button 94 of the blockage sensor 92 may have a number of components including a compressible overlay 144 with a conductor facing a contact extension 146 of the circuit board 138. Thus, when the compressible overlay 144 is pressed against the contact extension 146, electrical contact is made between two separate conductors on the contact extension 146 to close the circuit. The blockage sensor 92 also has a cover 148 that protrudes into a position facing the arcuate wall 90. The cover 148 may cover the compressible overlay 144 and the contact extension 146 to keep them from external interference. If desired, the cover 148 may be formed of a nonconductive, resilient material such as rubber.

The first portion 68 of the reservoir retainer 64 has a first cavity (not visible in FIG. 4) and a second cavity 150 through which the second reservoir 66 extends. The second cavity 150 has a generally arcuate shape that exposes the end and a portion of the side wall of the second reservoir, thereby permitting a user to easily access the second reservoir 66 to compress it along the longitudinal direction 40. Due to the resiliency of the side walls of the second reservoir 66, the second reservoir 66 will tend to expand, thereby providing a vacuum acting through the aspiration catheter 18 to draw fluid from the internal wound site 12.

The second portion 70 of the reservoir retainer 64 has a first cavity 152 and a second cavity 154. The second cavity 154 of the second portion 70 cooperates with the second cavity 150 of the first portion 68 to receive the second reservoir 66. The first cavity 152 of the second portion 70 cooperates with the first cavity of the first portion 68 to receive a first reservoir 156 that holds the medication to be infused into the internal wound site 12. Either of the first and second reservoirs 156, 66 may optionally be removable from the reservoir retainer 64 via relative motion in the longitudinal direction 40.

In addition to the tube 80, the reservoir module 48 has an aspiration conduit, which may take the form of a tube 158 that extends generally along the longitudinal direction 40. The tube 158 may be generally embedded within the first and second portions 68, 70 of the reservoir retainer 64, and may lead from the aspiration port 74 to the second reservoir 66. The tube 158 may be accessible through a slot 160 formed in the first and second portions 68, 70. Thus, the solenoid unit 142 may apply pressure to the tube 158 through the slot 160 to at least partially block fluid aspiration through the tube 158. In alternative embodiments, the tube 158 may also be arranged along a variety of different pathways.

If desired, the tube 158 may have a longitudinally oriented internal feature, such as a monofilament stitch (not shown), that is positioned proximate the point at which the solenoid unit 142 contacts the tube 158 to limit compression of the tube 158. Thus, the solenoid unit 142 may be able to dramatically decrease, but not entirely, stop, fluid aspiration from the internal wound site 12.

Assembly of the infusion unit 14 is relatively simple, and may be performed according to a variety of methods. According to one example, the circuit board 138, the motor 140, and the solenoid unit 142 may be inserted generally along the longitudinal direction 40 into the second portion 58 of the main body 52 of the controller 46 and attached to the second portion 58, to each other, or to some combination thereof. The compressible overlay 144 may be positioned against the contact extension 146, and the compressible overlay 144 and the contact extension 146 may be inserted into the cover 148. The first and second portions 56, 58 of the main body 52 may be aligned and moved together along the longitudinal direction 40, and attached together via screws, integrally formed snaps, rivets, or other known attachment devices.

The rotors 84 may be installed in the rotor carriage 86 and the rotor carriage 86 may then be attached to the exposed spindle of the motor 140. The cap 54 may be attached to the main body 52 to protect the rotor carriage 86 and the blockage sensor 92. The batteries 136 may be inserted into the open compartment, and the battery cover 134 may be attached to the remainder of the second portion 58 of the main body 52 to complete assembly of the controller 46.

The tubes 80, 158 may be coupled to the various ports 72, 74, 76 and to the corresponding reservoirs 66, 156. The first and second reservoirs 66, 156 may be seated in the first cavity and the second cavity 150, respectively, of the first portion 68 of the reservoir retainer 64, in the first and second cavities 152, 154 of the second portion 70 of the reservoir retainer 64, respectively, or in some combination thereof. The ports 72, 74, 76 are installed in the first portion 68, and the tubes 80, 158 are then arranged as shown in FIG. 4. The first and second portions 68, 70 are then aligned and moved together along the longitudinal direction 40, and attached together via screws, integrally formed snaps, rivets, or other known attachment devices to complete assembly of the reservoir module 48. The first reservoir 156 may be filled with medication after assembly via the fill port 76.

Once the controller 46 and the reservoir module 48 have been assembled, they may easily be coupled together to permit use of the infusion unit 14. According to one assembly method, the cap 54 of the controller 46 is first removed from the main body 52. The reservoir module 48 is then displaced from the controller along the longitudinal direction 40, as illustrated in FIG. 3, such that the second end 126 of the central recess 114 is adjacent to the first end 120 of the central plateau 112. The central plateau 112 is aligned with the central recess 114 and inserted into the central recess 114 along the longitudinal direction 40. The central plateau 112 slides into the central recess 114 until the nub of the central plateau 112 slides into engagement with the locking recess 128 of the central recess 114.

The controller 46 and the reservoir module 48 are then in the properly assembled relative configuration shown in FIG. 2. The reservoir module 48, and both of the reservoirs 156, 66 are all positioned alongside the motor 140. This means that some part of the reservoir module 48 is offset from some part of the motor 140 with a displacement that has no longitudinal component.

The tube 80 may then be stretched and inserted longitudinally to fit around the rotors 84 retained by the rotor carriage 86. A portion of the tube 80 is inserted between the arcuate wall 90 and the blockage sensor 92. The tube 80 may then be released so that the tube 80 is tightly routed about the rotors 84. The cap 54 may then be re-attached to the main body 52 to enclose the tube 80, rotors 84, rotor carriage 86, and blockage sensor 92.

Once the controller 46 and the reservoir module 48 have been attached together, the proximal ends 22, 28 of the catheters 16, 18 may be attached to the infusion port 72 and the aspiration port 74, respectively. The distal ends 24, 30 of the catheters 16, 18 are positioned in the internal wound site 12 through the point-of-entry 20. The distal ends 24, 30 may advantageously be positioned on opposite sides of the internal wound site 12 to enhance medication flow across the internal wound site 12.

When the controller 46 is activated, the motor 140 drives the pump 82 to draw medication from the first reservoir 156. The medication is drawn through the tube 80 and separated into discrete quantities due to the compression of the tube 80 proximate the rotors 84. The rotor carriage 86 rotates to move each bolus of medication through the tube 80 and out of the infusion unit 14 via the infusion port 72. The medication then moves to the internal wound site 12 via the infusion catheter 16. Fluids may simultaneously be removed from the internal wound site 12 in a similar manner via the interaction of the solenoid unit 142 with the tube 158. The controller 46 may operate according to a variety of schemes, for example, by providing a quantity of medication periodically, by providing medication on demand (within limits), or the like.

The system 10 of FIG. 1 is only one embodiment of an infusion system according to the present invention. Alternative embodiments may utilize a wide variety of different pumps, reservoir shapes and positions, and overall shapes and sizes of an infusion unit may be used. According to one alternative embodiment, an infusion system need not provide aspiration, but may only provide infusion of the internal wound site 12. Such an embodiment will be shown and described in connection with FIGS. 5 and 6, as follows.

Figure 5:
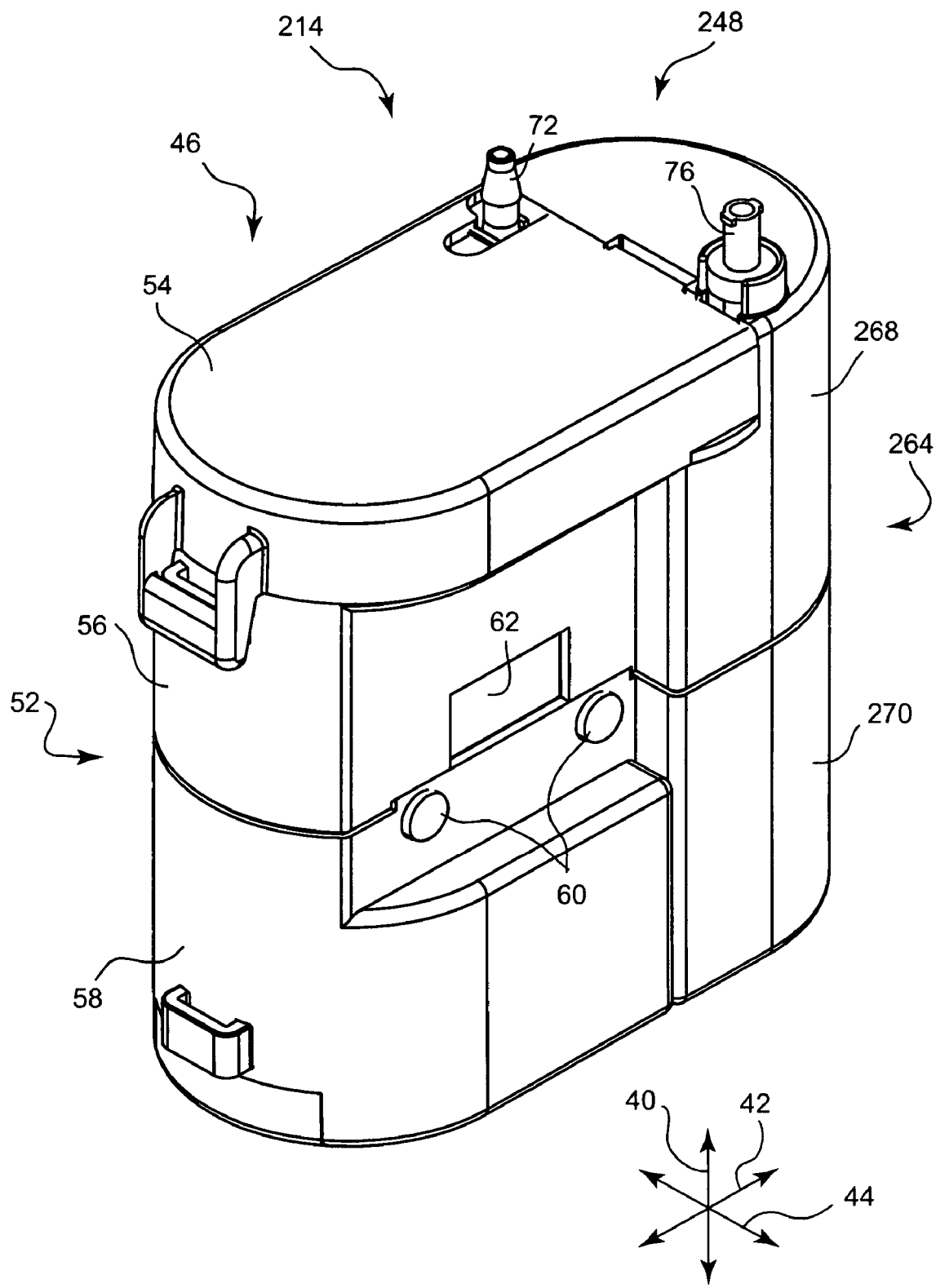
FIG. 5 is a perspective view of an infusion unit of an infusion system according to one alternative embodiment of the invention.

Referring to FIG. 5, a perspective view illustrates an infusion unit 214 according to one alternative embodiment of the invention. The infusion unit 214 does not aspirate the internal wound site 12, but may be connected to the internal wound site 12 to provide medication infusion via an infusion catheter 16 like that of FIG. 1.

As shown, the infusion unit 214 has a controller 46, which may be identical to the controller 46 illustrated in FIG. 2, and a reservoir module 248, which is somewhat different from the reservoir module 48 of FIG. 2. More precisely, the reservoir module 248 is designed only to provide medication for infusion, not to receive fluids aspirated from the internal wound site 12. Accordingly, the reservoir module 248 has a reservoir retainer 264 that is somewhat more compact than the reservoir retainer 64 of the previous embodiment. The reservoir retainer 264 may be separated into a first portion 268 and a second portion 270. The reservoir retainer 264 contains only a first reservoir (not shown in FIG. 5) that contains medication for infusion. Additionally, the reservoir module 248 has an infusion port 72 and a fill port 76 like those of the previous embodiment. However, no aspiration port is present.

Figure 6:
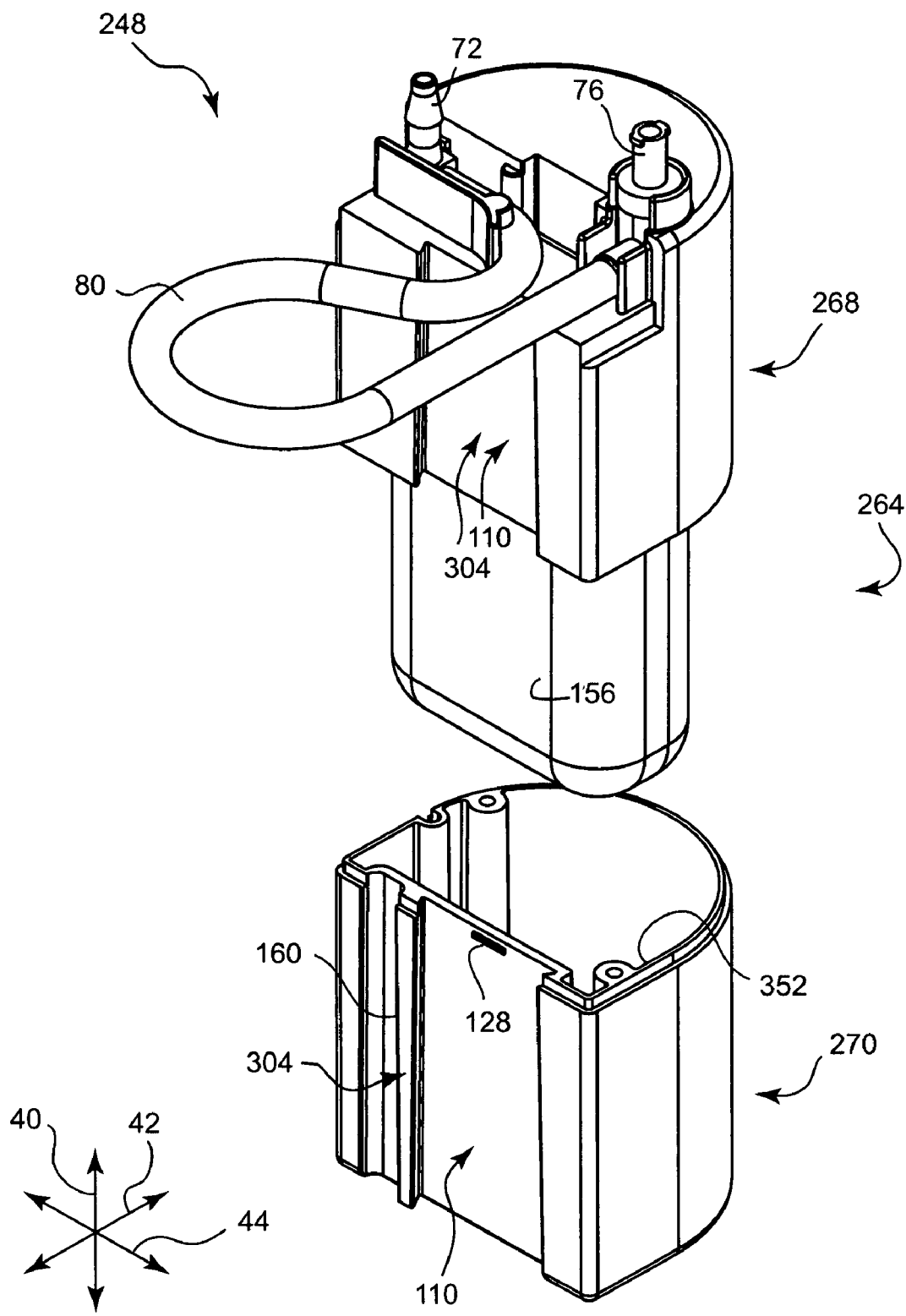
FIG. 6 is an exploded, perspective view of the reservoir module of the infusion unit of FIG. 5.

Referring to FIG. 6, an exploded, perspective view illustrates the reservoir module 248 of the infusion unit 214 in greater detail. As shown, the reservoir module 248 has a configuration somewhat similar to that of the reservoir module 48 of the previous embodiment. The reservoir retainer 264 has a mating surface 304 that is similar to the mating surface 104 of the reservoir retainer of the previous embodiment 64, except that all or part of the slot 160 may be omitted from the mating surface 304 because there is no tube 158 for aspiration. However, the mating surface 304 is still able to mate with the mating surface 102 of the controller 46 because the mating surface 304 has a dovetail feature 110 identical to that of the mating surface 104.

Like the dovetail feature 110 of the previous embodiment, the dovetail feature 110 of the reservoir module 248 is tapered to mate with the dovetail feature 108 of the controller 46 along only one direction. The dovetail feature 110 of the reservoir module 248 has a locking recess like the locking recess 48 of the previous embodiment. Accordingly, the method by which the reservoir module 248 is coupled to the controller 46 may be identical to that used to attach the reservoir module 48 to the controller 46.

The first portion 268 of the reservoir retainer 264 has a first cavity that receives part of the first reservoir 156. Similarly, the second portion 270 of the reservoir retainer 264 has a first cavity 352 that receives the remainder of the first reservoir 156. The first reservoir 156 may be the same as that of the previous embodiment.

The reservoir module 248 may be assembled in a manner similar to that described previously, in connection with the reservoir module 48. However, no aspiration port, second reservoir, or aspiration tube need be installed. The first and second portions 268, 270 are simply moved together along the longitudinal direction 40 and attached together to retain the first reservoir 156. The reservoir module 248 is then ready for use and may be coupled to the controller 46 via application of the method described in connection with the previous embodiment. Use of the infusion unit 214 is also similar to that described previously, in connection with the discussion of the infusion unit 14, except that no aspiration catheter is used, and aspiration is not performed.

Since either of the reservoir modules 48, 248 is capable of mating with the controller 46, the controller 46, reservoir module 48, and reservoir module 248 may form a kit of interchangeable parts that can be used for a variety of pain relief situations. For example, if aspiration is desired, the reservoir module 48 may be coupled to the controller 46 to form the infusion unit 14. If no aspiration is desired, the reservoir module 248 may be coupled to the controller 46 to form the infusion unit 214. The reservoir module 248 provides a lighter, more compact infusion unit 214 for situations in which aspiration is not needed.

The present invention may be embodied in other specific forms without departing from its spirit or essential characteristics. Thus the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A system for percutaneous infusion of an internal wound site, the system comprising:
    a first reservoir contained by a rigid housing, wherein the first reservoir is shaped to contain a first fluid;
    a controller comprising a motor and a peristaltic pump driven by the motor to urge the first fluid toward the internal wound site, the motor having an axis of rotation;
    a tube configured to engage the peristaltic pump to convey the first fluid, wherein the tube is coupled to the rigid housing at two locations along a length of the tube; and
    a catheter configured to convey the first fluid from the tube to the internal wound site and to infuse the first fluid into the internal wound site;
    wherein, in response to motion of the first reservoir along an attachment plane, the first reservoir is attachable to the controller to position the first reservoir alongside the motor;
    wherein the attachment plane is substantially parallel to at least one of the axis of rotation and an output shaft coupled to the motor to drive a pump.

2. The system of claim 1, wherein the controller further comprises a mating surface parallel to the attachment plane, wherein the first reservoir is coupled to a mating surface shaped to mate with the mating surface of the controller, wherein each of the mating surfaces has a generally planar shape.

3. The system of claim 2, wherein the mating surface of the controller extends alongside the motor and is oriented substantially parallel to the axis of rotation.

4. The system of claim 3, wherein the mating surface of the controller has a dovetail feature shaped to mate with a dovetail feature of the mating surface coupled to the first reservoir in response to sliding of the mating surfaces against each other to restrict withdrawal of the mating surfaces from each other along a direction generally perpendicular to the axis of rotation.

5. The system of claim 4, wherein the dovetail feature of one of the mating surfaces comprises a central plateau having two flared edges, wherein the dovetail feature of the other of the mating surfaces comprises a central recess shaped to receive the central plateau in interlocking fashion.

6. The system of claim 5, wherein each of the central plateau and the central recess tapers along the attachment plane such that clearance between the central plateau and the central recess decreases as the first reservoir moves toward a fully interlocked position with respect to the controller.

7. The system of claim 6, wherein one of the mating surfaces comprises a locking recess and the other of the mating surfaces comprises a nub shaped to slide into engagement with the locking recess to keep the first reservoir in the fully interlocked position with respect to the controller until a threshold level of force is applied to remove the nub from engagement with the locking recess.

8. The system of claim 1, wherein the peristaltic pump comprises a plurality of rotors that rotate about the axis to urge the first fluid to move through the tube.

9. The system of claim 8, wherein the tube is routed tightly about the rotors such that tension in the tube causes opposing sides of the tube to press against each other proximate each of the rotors to impede flow of the first fluid past the rotors.

10. The system of claim 8, wherein the peristaltic pump is configured to deliver a bolus of the first fluid to the internal wound site at a gage pressure of at least ten psi.

11. The system of claim 8, wherein the controller further comprises a blockage sensor that measures preferential distention of the tube along a direction perpendicular to the tube to determine whether the tube is blocked.

12. The system of claim 1, further comprising a second reservoir shaped to contain a second fluid, wherein the controller is further configured to aspirate the internal wound site by urging the second fluid into the second reservoir from the internal wound site.

13. A system for percutaneous infusion of an internal wound site, the system comprising:
a motor operable to urge a first fluid from a first reservoir through a tube toward the internal wound site, the motor having an axis of rotation; and
a mating surface extending alongside the motor, to receive a rigid housing containing the first reservoir in response to motion of the rigid housing along an attachment plane substantially parallel to at least one of the axis of rotation and an output shaft coupled to the motor to drive a pump;
wherein the motor is further operable to urge a second fluid from the internal wound site to a second reservoir;
wherein the tube is configured to engage the pump to convey the first fluid, wherein the tube is coupled to the rigid housing at two locations along a length of the tube.

14. The system of claim 13, wherein the mating surface has a generally planar shape.

15. The system of claim 14, wherein the mating surface has a dovetail feature shaped to mate with a dovetail feature of a mating surface of the rigid housing in response to sliding of the mating surfaces against each other to restrict withdrawal of the mating surfaces from each other along a direction generally perpendicular to the axis of rotation.

16. The system of claim 15, wherein the dovetail feature of one of the mating surfaces comprises a central plateau having two flared edges, wherein the dovetail feature of the other of the mating surfaces comprises a central recess shaped to receive the central plateau in interlocking fashion.

17. The system of claim 13, wherein the pump comprises a peristaltic pump driven by the motor, the peristaltic pump comprising a plurality of rotors that rotate about the axis to urge the first fluid to move through the tube.

18. The system of claim 17, wherein the tube is routed tightly about the rotors such that tension in the tube causes opposing sides of the tube to press against each other proximate each of the rotors to impede flow of the first fluid past the rotors.

19. The system of claim 17, wherein the peristaltic pump is configured to deliver a bolus of the first fluid to the internal wound site at a gage pressure of at least ten psi.

20. The system of claim 17, wherein the controller further comprises a blockage sensor that measures preferential distention of the tube along a direction perpendicular to the tube to determine whether the tube is blocked.

21. A system for percutaneous infusion of an internal wound site, the system comprising:
a first reservoir module comprising a first reservoir connectable to supply a first fluid to the internal wound site, and a rigid housing shaped to retain the first reservoir exclusively of any other reservoir connectable to provide fluid communication with the internal wound site;
a second reservoir module comprising a first reservoir connectable to supply the first fluid to infuse the internal wound site, and a second reservoir connectable to receive a second fluid aspirated from the internal wound site;
a controller matable to either of the first and second reservoir modules exclusively of the other of the first and second reservoir modules such that the controller is able to urge the first fluid to flow toward the internal wound site, wherein the controller comprises a pump; and
a tube configured to engage the pump to convey the first fluid, wherein the tube is coupled to the rigid housing at two locations along a length of the tube.

22. The system of claim 21, wherein the controller comprises a mating surface, wherein the second reservoir module further comprises a second reservoir retainer shaped to retain the first and second reservoirs of the second reservoir module, wherein each of the first and second reservoir modules comprises a mating surface matable with the mating surface of the controller.

23. The system of claim 22, wherein the pump is driven by a motor to urge the first fluid to flow toward the internal wound site, the motor having an axis of rotation, wherein the mating surface of the controller extends generally parallel to the axis of rotation, alongside the motor, to receive the mating surface of either of the first and second reservoir retainers in response to motion of the mating surface of either of the first and second reservoir retainers along an attachment plane substantially parallel to at least one of the axis of rotation and an output shaft coupled to the motor to drive the pump.

24. The system of claim 23, wherein the mating surface of the controller has a dovetail feature shaped to mate with a dovetail feature of the mating surfaces of each of the first and second reservoir modules in response to sliding of the mating surfaces against each other to restrict withdrawal of the mating surfaces from each other along a direction generally perpendicular to the axis of rotation.

25. The system of claim 21, wherein the pump comprises a peristaltic pump comprising a plurality of rotors that are rotatable to urge the first fluid to move through the tube leading toward the internal wound site.

26. The system of claim 25, wherein the controller comprises a second pump operable to urge the second fluid to move into the second reservoir.

27. The system of claim 21, wherein the first reservoir retainer comprises a cavity sized to slidably receive the first reservoir of the first reservoir module such that the first reservoir substantially fills the cavity, wherein, aside from the cavity, the first reservoir retainer is sufficiently solid to be incapable of receiving any other reservoir connectable to provide fluid communication with the internal wound site.

28. The system of claim 21, wherein the second reservoir module comprises a second reservoir retainer having a first cavity sized to slidably receive the first reservoir of the second reservoir module, and a second cavity sized to slidably receive the second reservoir of the second reservoir module.

29. A system for percutaneous infusion of an internal wound site, the system comprising:
- a reservoir module comprising a substantially rigid mating surface and a first reservoir contained by a rigid housing, wherein the first reservoir is shaped to contain a first fluid;
- a controller comprising a motor and a peristaltic pump driven by the motor to urge the first fluid toward the internal wound site, the motor having an axis of rotation, the controller further comprising a mating surface having a generally planar shape substantially parallel to the axis of rotation; and
- a tube configured to engage the peristaltic pump to convey the first fluid, wherein the tube is coupled to the rigid housing at two locations along a length of the tube;
- wherein the mating surface of the controller is shaped to receive the mating surface of the reservoir module in response to motion of the reservoir module along an attachment plane substantially parallel to at least one of the axis of rotation and an output shaft coupled to the motor to drive the peristaltic pump to position the first reservoir alongside the motor.

30. The system of claim 29, wherein the mating surface of the controller has a dovetail feature shaped to mate with a dovetail feature of the mating surface of the reservoir module in response to sliding of the mating surfaces against each other to restrict withdrawal of the mating surfaces from each other along a direction generally perpendicular to the axis of rotation, wherein the dovetail feature of one of the mating surfaces comprises a central plateau having two flared edges, wherein the dovetail feature of the other of the mating surfaces comprises a central recess shaped to receive the central plateau in interlocking fashion.

31. The system of claim 30, wherein each of the central plateau and the central recess tapers along the attachment plane such that clearance between the central plateau and the central recess decreases as the first reservoir moves toward a fully interlocked position with respect to the controller, wherein one of the mating surfaces comprises a locking recess and the other of the mating surfaces comprises a nub shaped to slide into engagement with the locking recess to keep the first reservoir in the fully interlocked position with respect to the controller until a threshold level of force is applied to remove the nub from engagement with the locking recess.

32. The system of claim 29, wherein the peristaltic pump comprises a plurality of rotors that rotate about the axis to urge the first fluid to move through the tube leading toward the internal wound site, wherein the tube is routed tightly about the rotors such that tension in the tube causes opposing sides of the tube to press against each other proximate each of the rotors to impede flow of the first fluid past the rotors.

33. The system of claim 32, wherein the peristaltic pump is configured to deliver a bolus of the first fluid to the internal wound site at a gage pressure of at least ten psi.

34. The system of claim 32, wherein the controller further comprises a blockage sensor that measures preferential distention of the tube along a direction perpendicular to the tube to determine whether the tube is blocked.

35. The system of claim 29, wherein the reservoir module further comprises a second reservoir shaped to contain a second fluid, wherein the controller is further configured to aspirate the internal wound site by urging the second fluid into the second reservoir from the internal wound site.

* * * * *

UNITED STATES PATENT AND TRADEMARK OFFICE
CERTIFICATE OF CORRECTION

PATENT NO. : 7,527,608 B2 Page 1 of 1
APPLICATION NO. : 10/909157
DATED : May 5, 2009
INVENTOR(S) : Jeffrey T. Mason It is certified that error appears in the above-identified patent and that said Letters Patent is hereby corrected as shown below:

Column 2, Line 6, DELETE "an" should be changed to --a--.

Column 5, Line 55, DELETE "fist" should be changed to --first--.

Column 7, Line 42, DELETE "," after entirely ADD "," after "stop" currently reads "but not entirely, stop, fluid" should read --but not entirely stop, fluid--.

Signed and Sealed this

Twenty-eighth Day of July, 2009

JOHN DOLL
*Acting Director of the United States Patent and Trademark Office*